United States Patent [19]

Faraj

[11] Patent Number: 5,288,919
[45] Date of Patent: Feb. 22, 1994

[54] PREPARATION OF DIALKYL PEROXIDES

[75] Inventor: Mahmoud K. Faraj, Newtown Square, Pa.

[73] Assignee: ARCO Chemical Technology, L.P., Wilmington, Del.

[21] Appl. No.: 61,139

[22] Filed: May 13, 1993

[51] Int. Cl.$^5$ ............................................. C07C 409/16
[52] U.S. Cl. ...................................... 568/578; 568/558
[58] Field of Search ................. 568/573, 574, 568, 578

[56] References Cited

U.S. PATENT DOCUMENTS

| | | | |
|---|---|---|---|
| 2,403,758 | 7/1946 | Rust et al. | 568/558 |
| 2,403,771 | 7/1946 | Vaughan et al. | 568/558 |
| 2,630,456 | 3/1953 | Bell et al. | 568/571 |
| 2,845,461 | 7/1958 | Winkler et al. | 568/571 |
| 2,862,973 | 12/1958 | Winkler et al. | 568/558 |
| 3,478,108 | 11/1969 | Grane | 568/571 |
| 3,626,014 | 12/1971 | Harvey | 568/571 |
| 3,833,664 | 9/1974 | Aoshima et al. | 568/578 |
| 3,947,332 | 3/1976 | Vanderpool et al. | 204/86 |
| 4,198,528 | 4/1980 | Kelsey | 568/578 |
| 4,266,081 | 5/1981 | Mizuno et al. | 568/578 |
| 4,408,081 | 10/1983 | Foster | 568/571 |
| 4,916,101 | 4/1990 | Lyons et al. | 502/209 |

OTHER PUBLICATIONS

"Organic Peroxides. Part III. The Preparation of Alkyl Hydroperoxides and Dialkyl Peroxides. Characteristic Derivatives of Alkyl Hydroperoxides." Davies, et al., J. Chem. Sec., pp. 2200–2204 (1954).

Primary Examiner—Werren B. Lone
Attorney, Agent, or Firm—William C. Long

[57] ABSTRACT

The present invention provides a process for the production of dialkyl peroxides by reaction of an alcohol and/or an olefin with an organic hydroperoxide, using an inorganic heteropoly and/or isopoly acid catalyst.

9 Claims, No Drawings

PREPARATION OF DIALKYL PEROXIDES

BACKGROUND OF THE INVENTION

1. Field of the Invention

The present invention relates to the production of dialkyl peroxides such as ditertiary butyl peroxide by the reaction of an alcohol such as tertiary butyl alcohol and/or an olefin such as isobutylene with a hydroperoxide such as tertiary butyl hydroperoxide in the presence of an inorganic heteropoly and/or isopoly acid catalyst.

2. Description of the Prior Art

The preparation of dialkyl peroxides by the reaction of an alcohol such as tertiary butyl alcohol (TBA) with an organic hydroperoxide such as tertiary butyl hydroperoxide (TBHP) is known. See, for example, U.S. Pat. Nos. 2,403,771, 2,403,758, 2,862,973, 3,626,014 and the like. The preparation of dialkyl peroxides by the reaction of an olefin such as 2-methylbut-2-ene with an organic hydroperoxide such as TBHP is also known. See Davies, et al., J. Chem. Sec. page 2200, 1954.

In such prior processes, catalysts such as sulfuric acid, sulfonic acid resins and the like have been employed. The use of such catalysts has a number of disadvantages including the corrosion and safety hazards associated with the use of sulfuric acid, catalyst deactivation and deterioration associated with the use of catalyst resins and the like. Canadian Patent 839,312, for example, shows the production of ditertiary butyl peroxide by the reaction of TBA with TBHP using a sulfonic acid resin with the requirement that water be azeotropically removed.

The preparation of organic hydroperoxides by reaction of an alcohol such as TBA with hydrogen peroxide using an inorganic heteropoly acid is shown in U.S. Pat. No. 2,630,456.

BRIEF DESCRIPTION OF THE INVENTION

In accordance with the present invention, a process is provided for the production of dialkyl peroxides wherein an alcohol and/or an olefin is reacted with an organic hydroperoxide in the presence of an inorganic heteropoly or isopoly acid catalyst.

DETAILED DESCRIPTION

The process of the present invention can be represented by the following equations:

$$ROH + R_1OOH \longrightarrow ROOR_1 + H_2O \quad (1)$$

or

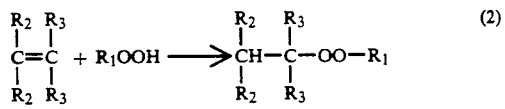

$$\begin{array}{c} R_2 \; R_3 \\ | \; \; | \\ C=C \\ | \; \; | \\ R_2 \; R_3 \end{array} + R_1OOH \longrightarrow \begin{array}{c} R_2 \; R_3 \\ | \; \; | \\ CH-C-OO-R_1 \\ | \; \; | \\ R_2 \; R_3 \end{array} \quad (2)$$

wherein R and $R_1$ are the same or different alkyl groups having 1 to 10 carbon atoms, $R_2$ and $R_3$ are hydrogen or R. Preferably, R and $R_1$ are the same tertiary alkyl group having 4 or 5 carbon atoms, i.e. tertiary butyl or tertiary amyl groups, $R_2$ is R and $R_3$ is hydrogen.

In especially preferred practice of the invention, ditertiary butyl peroxide is prepared by the reaction of tertiary butyl hydroperoxide with tertiary butyl alcohol and/or isobutylene, and ditertiary amyl hydroperoxide is prepared by the reaction of tertiary amyl hydroperoxide with tertiary amylene. Dialkyl peroxides where the alkyl groups are different, such as tertiary butyl tertiary amyl peroxide, can be prepared for example by reacting tertiary amyl alcohol and/or tertiary amylene with tertiary butyl hydroperoxide.

In carrying out the process of the present invention, it is generally desirable to provide at least 0.5 mols of alcohol and/or olefin per mol of hydroperoxide to the reaction. Preferably, at least 1 mol of alcohol and/or olefin per mol of hydroperoxide is employed up to about 5 mols of alcohol and/or olefin per mol of hydroperoxide. The use of alcohol and/or olefin in at least equimolar amounts relative to the hydroperoxide provides good reaction rates and high conversions of the reactants.

The reaction of the invention can be carried out using either alcohol or olefin to react with the hydroperoxide. Preferably, however, mixtures of 0.1 to 10 mols of alcohol per mol of olefin are employed.

The process of the invention is carried out at temperatures sufficiently high to ensure a satisfactory reaction rate but not so high as to cause substantial decomposition of the hydroperoxide. Generally, temperatures ranging from about 20° C. to 150° C. and preferably 40° C. to about 110° C. are employed. The reaction takes place in the liquid phase, and the system pressure is maintained at a level sufficient to ensure the liquid phase reaction. Pressures in the range 0.2 to 100 atmospheres gauge are illustrative.

Essential to practice of the invention is the use of an inorganic heteropoly and/or isopoly acid as catalyst. Such catalysts are water soluble, are highly stable, and are extremely active in promoting the process of the invention. Safety hazards and catalyst deterioration which were encountered in prior art procedures are substantially avoided through the use of these heteropoly or isopoly acid catalysts.

As a class, inorganic heteropoly and isopoly acids and their preparation are by now quite well known. See, for example, "Heteropoly and Isopoly Oxo-metalates", Pope, et al., Springer-Verlag, New York, 1983 the content of which is incorporated herein by reference. In this regard, reference is also made to U.S. Pat. No. 4,916,101, the disclosure of which is incorporated herein by reference, which describes the preparation of heteropoly acid catalysts useful in practice of the present invention. Similarly, U.S. Pat. No. 2,630,456 also describes heteropoly acids useful in catalyzing the reaction of hydrogen peroxide with alcohols to produce hydroperoxides, and the description of heteropoly acids contained therein is also incorporated by reference in the instant case. U.S. Pat. No. 3,947,332 shows preparation of the heteropoly acids also.

Heteropoly acids which are employed in practice of the invention are formed by the condensation of two or more inorganic oxyacids. For example, phosphate and tungstate ions, when reacted in an acidic medium, are condensed to form 12-tungstophosphoric acid, a typical heteropoly acid. In order to function as catalysts in accordance with the invention, the heteropoly anion must be associated with at least one hydrogen cation and preferably all of the cations are hydrogen.

Heteropoly acids of the Keggin structure are most common and are suitable for use in practice of the invention. Acids of the Dawson structure and of other structures can be used.

Illustrative heteropoly acids contain polyatoms selected from molybdenum, tungsten, niobium and vanadium, while the heteroatoms may be phosphorus, boron, germanium, antimony or silicon or the like. Illustrative heteropoly acids include 12-molybdophosphoric acid, 12-tungstophosphoric acid, 12-molybdosilica acid, and 12-tungstosilicic acid.

Isopoly acids having vanadate, niobate, molybdate and tungstate anions can be used. Examples are $H_6 (H_2W_{12}O_{40})$, $Na_3 H_3 V_{10} O_{28}$, $Na_4 H_5 Nb_9 O_{27}$ and $Na_7 H Nb_6 O_{19}$. Isopoly acids having mixed isopoly anions can be used.

In practice of the invention sufficient of the heteropoly or isopoly acid catalyst is employed to ensure a satisfactory conversion and selectivity. Generally, amounts of catalyst ranging from about 0.1 wt. % to about 20 wt. %, preferably 0.5 wt. % to about 10 wt. % based on the weight of the reaction mixture are satisfactorily employed.

In an especially preferred embodiment of the invention, isobutane oxidate which is produced in accordance with known oxidation procedures and which is comprised mainly of TBA and TBHP, after removal of unreacted isobutane, is directly reacted to form ditertiary butyl peroxide in accordance with the invention. U.S. Pat. Nos. 2,845,461, 3,478,108 and 4,408,081 describe the isobutane oxidation.

In order to more clearly illustrate the invention, the following examples are provided.

EXAMPLE 1

A debutanized isobutane oxidate is reacted in accordance with the invention to form DTBP. The oxidate contains about 58 wt. % TBA, about 40 wt. % TBHP, with the remainder comprised of methanol, acetone, water and traces of other organic materials. About 3.8 grams of the oxidate are combined with 0.2 grams of 12-tungstophosphoric acid catalyst and the mixture is heated to 80° C. under a nitrogen blanket ($H_3PW_{12}O_{40}$) After 6 hours reaction time, TBHP conversion was 82%, TBA conversion was 68% and the reaction selectivity to DTBP based on TBHP converted was 90%.

EXAMPLE 2

A series of runs was carried out in order to evaluate the effect of varying the TBA/TBHP mol ratio on DTBP formation. The catalyst employed was 12-tungstophosphoric acid, and the catalyst was used in amount of 10 wt. % based on the weight of the reaction mixture. In each case the reaction was carried out at 85° C. under a nitrogen blanket. The following table shows the results which were obtained.

TABLE 1

| TBA/TBHP mol ratio | Time hrs. | Conversion % TBHP | TBA | Selectivity* DTBP |
|---|---|---|---|---|
| 1.78 | 2 | 88 | 53 | 95 |
| 2.3 | 2 | 92 | 47.4 | 95.5 |
| 2.9 | 2 | 95 | 45 | 95 |

The above results show that higher conversions of the hydroperoxide are achieved as the ratio of alcohol to hydroperoxide is increased and that selectivity is reasonably constant.

EXAMPLE 3

Experimental runs were carried out to determine the effect of catalyst concentration on the reaction of the present invention. Isobutane oxidate as described in Example 1 was employed as was 12-tungstophosphoric acid catalyst. The runs were carried out at 85° C. under nitrogen and the following table shows the results which were obtained.

TABLE 2

| Catalyst wt. % | Time hrs. | Conversion % TBHP | TBA | Selectivity* DTBP |
|---|---|---|---|---|
| 5 | 2 | 70 | 42 | 93 |
| 10 | 2 | 88 | 53 | 95 |
| 20 | 1 | 95 | 70 | 94 |

*Based on TBHP converted.

As shown in the above table, the conversion increased with increasing catalyst concentrations, whereas the selectivity to the desired DTBP product remained essentially constant.

EXAMPLE 4

Experimental runs were carried out to determine the effect of isobutylene addition on the reaction of the present invention. Isobutane oxidate as described in Example 1 was employed as was 12-tungstophosphoric acid catalyst. The runs were carried out at 85° C. under nitrogen and the following table shows the results which were obtained.

TABLE 3

| Catalyst wt. % | Time hrs. | i-C$_4$/TBHP mol ratio | Conversion % TBHP | TBA | Selectivity* DTBP |
|---|---|---|---|---|---|
| 1 | 2 | 0 | 50 | 29 | 93 |
| 1 | 2 | 0.56 | 61 | 35 | 90 |
| 1 | 2 | 1.2 | 84 | 41 | 89 |

*Based on TBHP converted.

As shown in the above table, TBHP and TBA conversion increased with increasing addition of isobutylene, whereas the selectivity to the desired TBHP product remained high.

I claim:

1. A process for the preparation of a dialkyl peroxide having the formula ROOR$_1$ which comprises reacting a reagent selected from the group consisting of an alcohol having the formula ROH, an olefin having the formula:

and mixtures in the liquid phase with a hydroperoxide having the formula R$_1$OOH, at a temperature of 20°–150° C. and at a pressure sufficient to maintain the liquid phase in the presence of an effective amount of an inorganic heteropoly or isopoly acid catalyst, in the above formulae R and R$_1$ are alkyl groups having 1 to 10 carbon atoms, and R$_2$ and R$_3$ are hydrogen or R.

2. A process for the preparation of ditertiary butyl peroxide which comprises reacting a reagent selected from the group consisting of tertiary butyl alcohol, isobutylene, and mixtures with tertiary butyl hydroperoxide in the liquid phase at a temperature of 20°–150° C. and at a pressure sufficient to maintain the liquid phase in the presence of an effective amount of an inorganic heteropoly or isopoly acid catalyst.

3. The process of claim 2 wherein the catalyst is an inorganic heteropoly acid catalyst.

4. The process of claim 2 wherein the catalyst is 12-tungstophosphoric acid.

5. The process of claim 2 wherein a mixture of tertiary butyl alcohol and isobutylene containing 0.1 to 10 mols tertiary butyl alcohol per mol of isobutylene is reacted with tertiary butyl hydroperoxide.

6. A process for the preparation of ditertiary amyl peroxide which comprises reacting a reagent selected from the group consisting of tertiary amyl alcohol, isoamylene and mixtures with tertiary amyl hydroperoxide in the liquid phase at a temperature of 20°–150° C. and at a pressure sufficient to maintain the liquid phase in the presence of an effective amount of an inorganic heteropoly or isopoly acid catalyst.

7. The process of claim 6 wherein the catalyst is an inorganic heteropoly acid catalyst.

8. The process of claim 6 wherein the catalyst is 12-tungstophosphoric acid.

9. The process of claim 6 wherein a mixture of tertiary amyl alcohol and isoamylene containing 0.1 to 10 mols tertiary amyl alcohol per mol of isoamylene is reacted with tertiary amyl hydroperoxide.

* * * * *